United States Patent
Liang et al.

(10) Patent No.: US 11,439,984 B2
(45) Date of Patent: Sep. 13, 2022

(54) SUPPORTED MIXED OXIDES CATALYSTS FOR OXIDATIVE COUPLING OF METHANE

(71) Applicant: Sabic Global Technologies, B.V., Bergen op Zoom (NL)

(72) Inventors: Wugeng Liang, Sugar Land, TX (US); Luanyi Li, Sugar Land, TX (US); Hector Perez, Sugar Land, TX (US); Jae Hyung Kim, Sugar Land, TX (US); Pankaj Gautam, Sugar Land, TX (US); Vidya Sagar Reddy Sarsani, Sugar Land, TX (US); David West, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 205 days.

(21) Appl. No.: 16/821,409

(22) Filed: Mar. 17, 2020

(65) Prior Publication Data
US 2020/0298209 A1 Sep. 24, 2020

Related U.S. Application Data

(60) Provisional application No. 62/820,643, filed on Mar. 19, 2019.

(51) Int. Cl.
*B01J 23/10* (2006.01)
*B01J 35/00* (2006.01)
(Continued)

(52) U.S. Cl.
CPC .............. *B01J 23/10* (2013.01); *B01J 21/12* (2013.01); *B01J 35/0026* (2013.01);
(Continued)

(58) Field of Classification Search
CPC ........ B01J 23/10; B01J 21/12; B01J 35/0026; B01J 35/1009; B01J 35/1014;
(Continued)

(56) References Cited

U.S. PATENT DOCUMENTS

| 5,712,217 A | 1/1998 | Choudhary et al. |
| 6,087,545 A | 7/2000 | Choudhary et al. |

(Continued)

FOREIGN PATENT DOCUMENTS

| EP | 3194070 A2 | 7/2017 |
| WO | 2016044428 A2 | 3/2016 |

OTHER PUBLICATIONS

Choudhary, Vasant R. et al., "Coupling of Exothermic and Endothermic Reactions in Oxidative Conversion of Natural Gas into Ethylene/Olefins over Diluted SrO/La2O3/SA5205 Catalyst", Industrial & Engineering Chemistry Research, 1997, pp. 3520-3527, vol. 36, No. 9, American Chemical Society.
(Continued)

*Primary Examiner* — Ali Z Fadhel
(74) *Attorney, Agent, or Firm* — Rodney B. Carroll; Conley Rose, P.C.

(57) ABSTRACT

A supported oxidative coupling of methane (OCM) catalyst comprising a support and an OCM catalytic composition characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states.

20 Claims, 4 Drawing Sheets

(51) Int. Cl.
*B01J 35/10* (2006.01)
*B01J 37/02* (2006.01)
*C07C 2/84* (2006.01)
*B01J 21/12* (2006.01)

(52) U.S. Cl.
CPC ....... *B01J 35/1009* (2013.01); *B01J 35/1014* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 35/1085* (2013.01); *B01J 37/0209* (2013.01); *C07C 2/84* (2013.01); *C07C 2521/12* (2013.01); *C07C 2523/02* (2013.01); *C07C 2523/10* (2013.01)

(58) Field of Classification Search
CPC ............... B01J 35/1038; B01J 35/1042; B01J 35/1061; B01J 35/1066; B01J 35/1071; B01J 35/1076; B01J 35/1085; B01J 37/0209; B01J 23/002; B01J 2523/00; B01J 35/002; C07C 2/84; C07C 2521/12; C07C 2523/02; C07C 2523/10; Y02P 20/52; Y02P 20/582
See application file for complete search history.

(56) References Cited

U.S. PATENT DOCUMENTS

| | | | | |
|---|---|---|---|---|
| 2016/0074844 | A1* | 3/2016 | Freer | C07C 5/48 502/201 |
| 2017/0014807 | A1* | 1/2017 | Liang | C07C 2/84 |
| 2017/0267605 | A1* | 9/2017 | Tanur | B01J 35/1004 |

OTHER PUBLICATIONS

Mulla, S.A.R. et al., "Oxidative conversion of ethane to ethylene over supported SrO-promoted Er2O3 catalyst", Journal of Molecular Catalysis A: Chemical, 2004, pp. 259-262, vol. 223, Elsevier B.V.

Choudhary, Vasant R. et al., "Oxidative Coupling of Methane over a Sr-Promoted La2O3 Catalyst Supported on a Low Surface Area Porous Catalyst Carrier", Industrial & Engineering Chemistry Research, 1997, pp. 3594-3601, vol. 36, No. 9, American Chemical Society.

Choudhary, Vasant R. et al., "Oxidative Coupling of Methane over Supported La2O3 and La-Promoted MgO Catalysts: Influence of Catalyst-Support Interactions", Industrial & Engineering Chemistry Research, 1997, pp. 2096-2100, vol. 36, No. 6, American Chemical Society.

Choudhary, V.R. et al., "Oxidative Coupling of Methane over SrO Deposited on Different Commercial Supports Precoated with La2O3", Industrial & Engineering Chemistry Research, 1998, pp. 2142-2147, vol. 37, No. 6, American Chemical Society.

Mulla, S.A.R. et al., "Conversion of ethane to ethylene in presence of limited O2 over supported SrO promoted Sm2O3 catalyst", Indian Journal of Chemical Technology, Nov. 2003, pp. 615-618, vol. 10.

Asami, Kenji et al., "Selective Oxidative Coupling of Methane over Supported Lead Oxide Catalyst," Chemistry Letters, 1986, pp. 1233-1236, The Chemical Society of Japan.

Uphade, B.S. et al., "Influence of metal oxide-Support interactions in supported la-promoted CaO catalysts for oxidative coupling of methane," Studies in Surface Science and Catalysis, 1998, pp. 1015-1021, vol. 113, Elsevier B.V. (Abstract Only).

Bytyn, W. et al., "Supported PbO catalysts for the oxidative coupling of methane—The effect of surface acidity of the support on C2+ selectivity," Applied Catalysis, 1986, pp. 199-207, vol. 28, Elsevier B.V. (Abstract Only).

Fang, Xueping et al., "Oxidative Coupling of Methane on W-Mn Catalysts," Journal of Molecular Catalysis, 1992, pp. 255-261, vol. 8, No. 4.

Fang, Xueping et al., "Preparation and Characterization of Catalyst for Oxidative Coupling of Methane," Journal of Molecular Catalysis, 1992, pp. 427-433, vol. 6, No. 6.

Lee, Jong Yeol et al., "Scaled-up production of C2 hydrocarbons by the oxidative coupling of methane over pelletized Na2WO4/Mn/SiO2 catalysts: Observing hot spots for the selective process," Fuel, 2013, pp. 851-857, vol. 106, Elsevier Limited.

Arndt, Sebastian et al., "Mn-Na2WO4/SiO2 as Catalyst for the Oxidative Coupling of Methane. What is Really Known?," Applied Catalysis A: General, 2012, pp. 53-61, vols. 425-426, Elsevier.

* cited by examiner

Un-supported

Supported

United States Patent US 11,439,984 B2

SUPPORTED MIXED OXIDES CATALYSTS FOR OXIDATIVE COUPLING OF METHANE

CROSS REFERENCE TO RELATED APPLICATIONS

This application claims priority to U.S. Provisional Application No. 62/820,643 filed on Mar. 19, 2019 and entitled "Supported Mixed Oxides Catalysts for Oxidative Coupling of Methane", which is incorporated by reference herein in its entirety.

TECHNICAL FIELD

The present disclosure relates to supported catalyst compositions for oxidative coupling of methane (OCM), more specifically supported catalyst compositions based on oxides of alkaline earth metals, and rare earth elements for OCM, and methods of making and using same.

BACKGROUND

Hydrocarbons, and specifically olefins such as ethylene, are typically building blocks used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes. Oxidative coupling of the methane (OCM) has been the target of intense scientific and commercial interest for more than thirty years due to the tremendous potential of such technology to reduce costs, energy, and environmental emissions in the production of ethylene ($C_2H_4$). As an overall reaction, in the OCM, methane ($CH_4$) and oxygen ($O_2$) react exothermically over a catalyst to form $C_2H_4$, water ($H_2O$) and heat.

Ethylene can be produced by OCM as represented by Equations (I) and (II):

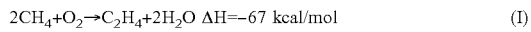

$$2CH_4 + O_2 \rightarrow C_2H_4 + 2H_2O \quad \Delta H = -67 \text{ kcal/mol} \quad (I)$$

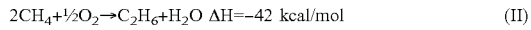

$$2CH_4 + \tfrac{1}{2}O_2 \rightarrow C_2H_6 + H_2O \quad \Delta H = -42 \text{ kcal/mol} \quad (II)$$

Oxidative conversion of methane to ethylene is exothermic. Excess heat produced from these reactions (Equations (I) and (II)) can push conversion of methane to carbon monoxide and carbon dioxide rather than the desired $C_2$ hydrocarbon product (e.g., ethylene):

$$CH_4 + 1.5O_2 \rightarrow CO + 2H_2O \quad \Delta H = -124 \text{ kcal/mol} \quad (III)$$

$$CH_4 + 2O_2 \rightarrow CO_2 + 2H_2O \quad \Delta H = -192 \text{ kcal/mol} \quad (IV)$$

The excess heat from the reactions in Equations (III) and (IV) further exasperate this situation, thereby substantially reducing the selectivity of ethylene production when compared with carbon monoxide and carbon dioxide production.

Additionally, while the overall OCM is exothermic, catalysts are used to overcome the endothermic nature of the C—H bond breakage. The endothermic nature of the bond breakage is due to the chemical stability of methane, which is a chemically stable molecule due to the presence of its four strong tetrahedral C—H bonds (435 kJ/mol). When catalysts are used in the OCM, the exothermic reaction can lead to a large increase in catalyst bed temperature and uncontrolled heat excursions that can lead to catalyst deactivation and a further decrease in ethylene selectivity. Furthermore, the produced ethylene is highly reactive and can form unwanted and thermodynamically favored deep oxidation products.

Generally, in the OCM, $CH_4$ is first oxidatively converted into ethane ($C_2H_6$), and then into $C_2H_4$. $CH_4$ is activated heterogeneously on a catalyst surface, forming methyl radicals (e.g., $CH_3$·), which then couple in a gas phase to form $C_2H_6$. $C_2H_6$ subsequently undergoes dehydrogenation to form $C_2H_4$. An overall yield of desired $C_2$ hydrocarbons is reduced by non-selective reactions of methyl radicals with oxygen on the catalyst surface and/or in the gas phase, which produce (undesirable) carbon monoxide and carbon dioxide. Some of the best reported OCM outcomes encompass a ~20% conversion of methane and ~80% selectivity to desired $C_2$ hydrocarbons.

There are many catalyst systems developed for OCM processes, but such catalyst systems have many shortcomings. For example, conventional catalysts systems for OCM display catalyst performance problems, stemming from a need for high reaction temperatures to achieve desired conversions and selectivities, while displaying unstable performance across wide temperature ranges. Thus, there is an ongoing need for the development of catalyst compositions for OCM processes.

BRIEF DESCRIPTION OF THE DRAWINGS

For a detailed description of the preferred aspects of the disclosed methods, reference will now be made to the accompanying drawing in which.

SUMMARY

Figure 1:
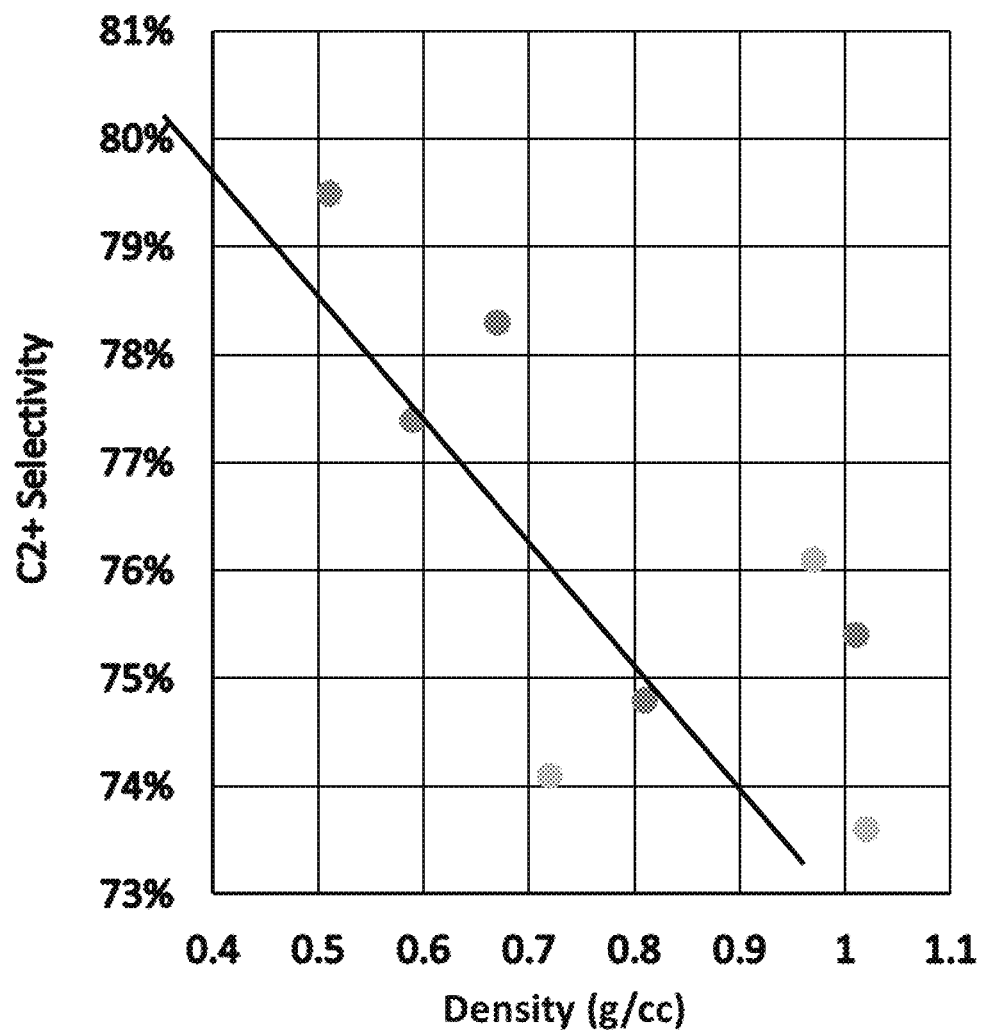
FIG. 1 is a plot of $C_{2+}$ selectivity as a function of density for unsupported OCM catalytic compositions.

Disclosed herein is a supported oxidative coupling of methane (OCM) catalyst comprising a support and an OCM catalytic composition characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states, wherein the supported OCM catalyst has a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc and wherein the catalyst has a $C_{2+}$ selectivity that satisfies the equation: $Y > -8X + 84$, where Y is the $C_{2+}$ selectivity and X is the density of the supported OCM catalyst in g/cc.

Also disclosed herein is a method of making a supported oxidative coupling of methane (OCM) catalyst comprising contacting a support with an OCM catalytic composition characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states, wherein the supported OCM catalyst has a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc and wherein the catalyst has a $C_{2+}$ selectivity that satisfies the equation: $y > -8x + 84$, where Y is the $C_{2+}$ selectivity and X is the density of the supported OCM catalyst in g/cc.

Further disclosed herein is a method for producing olefins comprising (i) introducing a reactant mixture to a reactor comprising the supported OCM catalyst of any of claims 1-17, wherein the reactant mixture comprises $CH_4$ and $O_2$, (ii) allowing at least a portion of the reactant mixture to contact at least a portion of the supported OCM catalyst and react via an OCM reaction to form a product mixture comprising unreacted methane and olefins, (iii) recovering at least a portion of the product mixture from the reactor; and (iv) optionally cooling the product mixture, wherein the reactor is operated a temperature in a range of from about 700° C. to about 1000° C., alternatively in a range of from about 750° C. to about 1000° C., alternatively in a range of from about 775° C. to about 950° C., alternatively in a range of from about 775° C. to about 850° C., or alternatively in a range of from about 800° C. to about 900° C., wherein the OCM reaction is characterized by (a) a $C_{2+}$ selectivity of equal to or greater than 75%, alternatively equal to or greater than 77%, or alternatively equal to or greater than 79%, (b) a methane conversion of equal to or greater than 15%, alternatively equal to or greater than 17%, or alternatively equal to or greater than 20%, (c) a $C_{2+}$ yield of equal to or greater than 12%, alternatively equal to or greater than 14%, or alternatively equal to or greater than 16%; or (d) combinations of (a), (b), and (c). In an aspect, the reactor temperature is a temperature measured, for example via a thermocouple, in a bed of the supported OCM catalyst disposed within the reactor.

Disclosed herein are supported oxidative coupling of methane (OCM) catalysts and methods of making and using same. In an aspect, a supported OCM catalyst comprises a support and an OCM catalytic composition characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states.

In an aspect, a method of making a supported oxidative coupling of methane (OCM) catalyst composition comprises contacting a support with an OCM catalytic composition characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states. The contacting can be performed via impregnation with an aqueous solution comprising the OCM catalytic composition to form an impregnated support, wherein the impregnated support is thermally treated to form the supported OCM catalyst.

In an aspect, a method for producing olefins as disclosed herein can comprise (i) introducing a reactant mixture (e.g., an OCM reactant mixture) to a reactor comprising a supported OCM catalyst composition, wherein the reactant mixture comprises methane ($CH_4$) and oxygen ($O_2$), and wherein the supported OCM catalyst composition comprises a support and an OCM catalytic composition characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states; and (ii) allowing at least a portion of the reactant mixture to contact at least a portion of the supported OCM catalyst and react via an OCM reaction to form a product mixture comprising unreacted methane and olefins.

DETAILED DESCRIPTION

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x s$" are interchangeable and refer to any hydrocarbon having x number of carbon atoms (C). For example, the terms "$C_4$ hydrocarbons" and "$C_4 s$" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3 s$, $C_4 s$, $C_5 s$, etc.

In an aspect, the supported OCM catalysts disclosed herein comprise a support and an OCM catalytic composition. The OCM catalytic composition disclosed herein can be characterized by the general formula $A_a Z_b E_c D_d O_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0, alternatively from about 0.3 to about 10.0, alternatively from about 0.5 to about 8, or alternatively from about 1 to about 5; wherein c is from about 0.1 to about 10.0, alternatively from about 0.1 to about 8, or alternatively from about 0.5 to about 5; wherein d is from about 0 to about 10.0, alternatively from about 0.1 to about 8, or alternatively from about 0.5 to about 5; and wherein x balances the oxidation states. As will be appreciated by one of the skill in the art, and with the help of this disclosure, each of the A, Z, E and D can have multiple oxidation states within the OCM catalystic composition, and as such x can have any suitable value that allows for the oxygen anions to balance all the cations. Without wishing to be limited by theory, the different metals (A, Z, E, and D) present in the OCM catalystic compositions as disclosed herein display synergetic effects in terms of conversion and selectivity. Further, and without wishing to be limited by theory, different ion radii and valences of the multiple metals (A, Z, E, and D) present in the OCM catalyst compositions as disclosed herein can generate formation of uncompensated oxygen vacancies, which can lead to further improvement of catalyst performance, for example in terms of conversion, selectivity, stability, etc.

The OCM catalytic composition as disclosed herein can comprise an alkaline earth metal (A). The alkaline earth metal (A) can be selected from the group consisting of magnesium (Mg), calcium (Ca), strontium (Sr), barium (Ba), and combinations thereof. In an aspect, the alkaline earth metal (A) is strontium (Sr).

The OCM catalytic composition as disclosed herein can comprise a first rare earth element (Z), wherein the first rare earth element (Z) can be selected from the group consisting of lanthanum (La), neodymium (Nd), promethium (Pm), samarium (Sm), europium (Eu), and combinations thereof. In an aspect, the first rare earth element (Z) is lanthanum (La). As will be appreciated by one of skill in the art, and with the help of this disclosure, in some aspects, the first rare earth element (Z) can comprise a single rare earth element, such as lanthanum (La). Further, and as will be appreciated by one of skill in the art, and with the help of this disclosure, in some aspects, the first rare earth element (Z) can comprise two or more rare earth elements, such as lanthanum (La), and neodymium (Nd), for example; or lanthanum (La), neodymium (Nd), and promethium (Pm), as another example; etc.

The OCM catalytic composition as disclosed herein can comprise a second rare earth element (E) and/or a third rare earth element (D), wherein E and D are different. The second rare earth element (E) and the third rare earth element (D) can each independently be selected from the group consisting of lanthanum (La), scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

As will be appreciated by one of skill in the art, and with the help of this disclosure, in some aspects, the second rare earth element (E) can comprise a single rare earth element, such as ytterbium (Yb). Further, and as will be appreciated by one of skill in the art, and with the help of this disclosure, in some aspects, the second rare earth element (E) can comprise two or more rare earth elements, such as ytterbium (Yb), and neodymium (Nd), for example; or ytterbium (Yb), and thulium (Tm), as another example; or ytterbium (Yb), neodymium (Nd), and thulium (Tm), as yet another example; etc.

As will be appreciated by one of skill in the art, and with the help of this disclosure, in some aspects, the third rare earth element (D) can comprise a single rare earth element, such as ytterbium (Yb). Further, and as will be appreciated by one of skill in the art, and with the help of this disclosure, in some aspects, the third rare earth element (D) can comprise two or more rare earth elements, such as ytterbium (Yb), and neodymium (Nd), for example; or ytterbium (Yb), neodymium (Nd), and promethium (Pm), as another example; etc.

The OCM catalytic composition as disclosed herein can comprise component (D). As will be appreciated by one of skill in the art, and with the help of this disclosure, D can be either a redox agent or a third rare earth element.

The redox agent (D) can be selected from the group consisting of manganese (Mn), tungsten (W), bismuth (Bi), antimony (Sb), tin (Sn), cerium (Ce), praseodymium (Pr), and combinations thereof. A redox agent generally refers to a chemical species that possesses the ability to undergo both an oxidation reaction and a reduction reaction, and such ability usually resides in the chemical species having more than one stable oxidation state other than the oxidation state of zero (0). As will be appreciated by one of skill in the art, and with the help of this disclosure, some rare earth elements, such as Ce and Pr, can also be considered redox agents. Further, as will be appreciated by one of skill in the art, and with the help of this disclosure, when D is Ce and/or Pr, D can be considered either a redox agent or a third rare earth element.

As will be appreciated by one of skill in the art, and with the help of this disclosure, in some aspects, the redox agent (D) can comprise a single element, such as manganese (Mn). Further, and as will be appreciated by one of skill in the art, and with the help of this disclosure, in some aspects, the redox agent (D) can comprise two or more compounds, such as manganese (Mn), and tungsten (W), for example; or manganese (Mn), tungsten (W), and praseodymium (Pr), as another example; etc. In some aspects, the redox agent (D) is manganese (Mn). In other aspects, the redox agent (D) is tungsten (W). In an aspect, the redox agent (D) excludes a rare earth element.

In an aspect, the second rare earth element (E) and/or the third rare earth element (D) can be basic (e.g., can exhibit some degree of basicity; can have affinity for hydrogen; can exhibit some degree of affinity for hydrogen). Nonlimiting examples of rare earth elements that can be considered basic for purposes of the disclosure herein include one or more compounds selected from the group consisting of scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof. As will be appreciated by one of skill in the art, and with the help of this disclosure, and without wishing to be limited by theory, the OCM reaction is a multi-step reaction, wherein each step of the OCM reaction could benefit from specific OCM catalytic properties. For example, and without wishing to be limited by theory, an OCM catalytic composition should exhibit some degree of basicity to abstract a hydrogen from $CH_4$ to form hydroxyl groups [OH] on the OCM catalytic composition surface, as well as methyl radicals ($CH_3 \cdot$). Further, and without wishing to be limited by theory, an OCM catalytic composition should exhibit oxidative properties for the OCM catalytic composition to convert the hydroxyl groups [OH] from the OCM catalytic composition surface to water, which can allow for the OCM reaction to continue (e.g., propagate). Furthermore, as will be appreciated by one of skill in the art, and with the help of this disclosure, and without wishing to be limited by theory, an OCM catalytic composition could also benefit from properties like oxygen ion conductivity and proton conductivity, which properties can be critical for the OCM reaction to proceed at a very high rate (e.g., its highest possible rate). Furthermore, as will be appreciated by one of skill in the art, and with the help of this disclosure, and without wishing to be limited by theory, an OCM catalytic composition comprising a single metal might not provide all the necessary properties for an optimum OCM reaction (e.g., best OCM reaction outcome) at the best level, and as such conducting an optimum OCM reaction may require an OCM catalytic composition with a tailored composition in terms of metals present, wherein the different metals can have optimum properties for various OCM reaction steps, and wherein the different metals can provide synergistically for achieving the best performance for the OCM catalytic composition in an OCM reaction.

In an aspect, the OCM catalytic composition as disclosed herein can comprise one or more oxides of A; one or more oxides of Z; one or more oxides of E; one or more oxides of D; or combinations thereof. The OCM catalyst composition can comprise one or more oxides of a metal, wherein the metal comprises A, Z, E, and optionally D. In some aspects, the OCM catalytic composition can comprise, consist of, or consist essentially of the one or more oxides of a metal, wherein the metal comprises A, Z, E, and optionally D.

In an aspect, the one or more oxides can be present in the OCM catalytic composition in an amount of from about 0.01 wt. % to about 100.0 wt. %, alternatively from about 0.1 wt. % to about 99.0 wt. %, alternatively from about 1.0 wt. % to about 95.0 wt. %, alternatively from about 10.0 wt. % to about 90.0 wt. %, or alternatively from about 30.0 wt. % to about 70.0 wt. %, based on the total weight of the OCM catalytic composition. As will be appreciated by one of skill in the art, and with the help of this disclosure, a portion of the one or more oxides, in the presence of water, such as atmospheric moisture, can convert to hydroxides, and it is possible that the OCM catalytic composition will comprise some hydroxides, due to exposing the OCM catalytic composition comprising the one or more oxides to water (e.g., atmospheric moisture). Further, as will be appreciated by one of skill in the art, and with the help of this disclosure, a portion of the one or more oxides, in the presence of carbon dioxide, such as atmospheric carbon dioxide, can convert to carbonates, and it is possible that the OCM catalytic composition will comprise some carbonates, due to exposing the OCM catalytic composition comprising the one or more oxides to carbon dioxide (e.g., atmospheric carbon dioxide).

The one or more oxides can comprise a single metal oxide, mixtures of single metal oxides, a mixed metal oxide, mixtures of mixed metal oxides, mixtures of single metal oxides and mixed metal oxides, or combinations thereof.

The single metal oxide comprises one metal selected from the group consisting of A, Z, E, and D. A single metal oxide can be characterized by the general formula $M_mO_y$; wherein M is the metal selected from the group consisting of A, Z, E, and D; and wherein m and y are integers from 1 to 7, alternatively from 1 to 5, or alternatively from 1 to 3. A single metal oxide contains one and only one metal cation. Nonlimiting examples of single metal oxides suitable for use in the OCM catalytic compositions of the present disclosure include $CaO$, $MgO$, $SrO$, $BaO$, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $W_2O_3$, $SnO_2$, and the like, or combinations thereof.

In an aspect, mixtures of single metal oxides can comprise two or more different single metal oxides, wherein the two or more different single metal oxides have been mixed together to form the mixture of single metal oxides. Mixtures of single metal oxides can comprise two or more different single metal oxides, wherein each single metal oxide can be selected from the group consisting of CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $W_2O_3$, and $SnO_2$. Nonlimiting examples of mixtures of single metal oxides suitable for use in the OCM catalyst compositions of the present disclosure include $SrO$—$La_2O_3$, $SrO$—$MgO$—$La_2O_3$, $SrO$—$Yb_2O_3$—$La_2O_3$, $SrO$—$Er_2O_3$—$La_2O_3$, $SrO$—$CeO_2$—$La_2O_3$, $SrO$—$MnO_2$—$La_2O_3$, $SrO$—$WO_3$—$W_2O_3$—$La_2O_3$, $SrO$—$WO_3$—$Tm_2O_3$—$La_2O_3$, $SrO$—$WO_3$—$Tm_2O_3$—$La_2O_3$, $SrO$—$BaO$—$CeO_2$—$Er_2O_3$—$La_2O_3$, $SrO$—$CeO_2$—$Ce_2O_3$—$Er_2O_3$—$La_2O_3$, $SrO$—$BaO$—$WO_3$—$W_2O_3$—$La_2O_3$, $SrO$—$BaO$—$Sm_2O_3$—$WO_3$—$W_2O_3$—$La_2O_3$, $SrO$—$MgO$—$CeO_2$—$Ce_2O_3$—$WO_3$—$W_2O_3$—$La_2O_3$, $SrO$—$CaO$—$PrO_2$—$Pr_2O_3$—$MnO$—$Mn_2MnO_3$—$La_2O_3$, and the like, or combinations thereof.

The mixed metal oxide comprises two or more different metals, wherein each metal can be independently selected from the group consisting of A, Z, E, and D. A mixed metal oxide can be characterized by the general formula $M^1_{m1}M^2_{m2}O_y$; wherein $M^1$ and $M^2$ are metals; wherein each of the $M^1$ and $M^2$ can be independently selected from the group consisting of A, Z, E, and D; and wherein m1, m2 and y are integers from 1 to 15, alternatively from 1 to 10, or alternatively from 1 to 7. In some aspects, $M^1$ and $M^2$ can be metal cations of different chemical elements, for example $M^1$ can be a lanthanum cation and $M^2$ can be a strontium cation. In other embodiments, $M^1$ and $M^2$ can be different cations of the same chemical element, wherein $M^1$ and $M^2$ can have different oxidation states. For example, the mixed metal oxide can comprise $Mn_3O_4$, wherein $M^1$ can be a Mn (II) cation and $M^2$ can be a Mn (III) cation. Nonlimiting examples of mixed metal oxides suitable for use in the OCM catalyst compositions of the present disclosure include La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of mixed metal oxides can comprise two or more different mixed metal oxides, wherein the two or more different mixed metal oxides have been mixed together to form the mixture of mixed metal oxides. Mixtures of mixed metal oxides can comprise two or more different mixed metal oxides, such as La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of single metal oxides and mixed metal oxides can comprise at least one single metal oxide and at least one mixed metal oxide, wherein the at least one single metal oxide and the at least one mixed metal oxide have been mixed together to form the mixture of single metal oxides and mixed metal oxides.

In an aspect, the supported OCM catalysts disclosed herein comprise a support, wherein one or more of the OCM catalytic compositions described herein are physically or structurally supported by the support such that the OCM catalytic compositions are provided with additional structural and/or mechanical strength (e.g., improved crush strength) in comparison to unsupported OCM catalyst compositions. In an aspect, the supported OCM catalyst comprises an OCM catalytic composition supported by a support, wherein at least a portion of the OCM catalytic composition contacts, coats, is embedded in, is supported by, and/or is distributed throughout at least a portion of the support.

In some aspects, the supported OCM catalyst can comprise a support, wherein the support can be catalytically inactive or inert (e.g., the support cannot catalyze an OCM reaction).

In an aspect, the support can be in the form of powders, particles, pellets, monoliths, foams, honeycombs, and the like, or combinations thereof. Nonlimiting examples of support particle shapes include cylindrical, discoidal, spherical, tabular, ellipsoidal, equant, irregular, cubic, acicular, and the like, or combinations thereof.

As will be appreciated by one of skill in the art, and with the help of this disclosure, the support can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In an aspect, the OCM catalyst composition can further comprise a porous support. As will be appreciated by one of skill in the art, and with the help of this disclosure, a porous material (e.g., support) can provide for an enhanced surface area of contact between the OCM catalytic composition and the reactant mixture, which in turn would result in a higher $CH_4$ conversion to $CH_3$.

The support can have a surface area in a range of from greater than zero and less than about 20.0 $m^2$/g, alternatively in a range of from greater than zero and less than about 10.0 $m^2$/g, or alternatively in a range of from greater than zero and less than about 5.0 $m^2$/g, as determined by measuring nitrogen adsorption according to the Brunauer, Emmett and Teller (BET) method.

The support can have a total pore volume in a range of from about 0.1 cc/g to about 1.0 cc/g, alternatively in a range of from about 0.15 cc/g to about 0.8 cc/g, or alternatively in a range of from about 0.2 cc/g to about 0.6 cc/g, as determined by measuring nitrogen adsorption according to the BET method.

The support can have a pore size distribution in a range of from about 0.01 microns to about 500 microns, alternatively in a range of from about 0.1 microns to about 100 microns, or alternatively in a range of from about 0.5 microns to about 50 microns, as determined by measuring nitrogen adsorption according to the BET method.

Nonlimiting examples of a support suitable for use in the present disclosure include, $Al_2O_3$ (alumina), $SiO_2$ (silica), silica-alumina ($SiO_2$—$Al_2O_3$), silica carbide, zirconia ($ZrO_2$), titania ($TiO_2$), magnesium oxide (MgO), zeolites, transition metal oxides, alkali metal oxides, alkaline earth metal oxides, lanthanide oxides, actinide oxides, carbon, and the like, or combinations thereof. In an aspect, the support is a silica-alumina ($SiO_2$—$Al_2O_3$). In an aspect, the support is alumina ($Al_2O_3$).

In an aspect, a supported OCM catalyst as disclosed herein can comprise a zeolitic support. For purposes of the disclosure herein the term "zeolitic support(s)" includes zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof. Further, for purposes of the disclosure herein, zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof are referred to herein collectively as "zeolites."

In an aspect, the support comprises silica-alumina and is characterized by a weight ratio of silica to alumina ($SiO_2$/$Al_2O_3$) of equal to or greater than about 0.02. In an aspect, the support comprises silica-alumina and is characterized by a weight ratio of silica to alumina ($SiO_2$/$Al_2O_3$) of equal to or greater than about 0.05. In an aspect, the support is a low acidity support.

The supported OCM catalyst (comprising a support and an OCM catalytic composition of the type described herein) can have any suitable desired particle specifications (e.g., crush strength, pressure drop across a catalyst bed, etc.), for example as required by a specific application. For example, the supported OCM catalyst can be characterized by a size suitable for use in a particular reactor (e.g., an OCM reactor having a particular catalyst bed configuration). As will be appreciated by one of skill in the art, and with the help of this disclosure, the supported OCM catalyst size can be determined for a particular application to achieve the best performance for the OCM reaction (e.g., desired conversion, desired selectivity, pressure drop, residence time, etc.).

The supported OCM catalyst as disclosed herein can comprise a support in an amount of from about 5 wt. % to about 95 wt. %, alternatively from about 25 wt. % to about 75 wt. %, or alternatively from about 35 wt. % to about 65 wt. %, based on the total weight of the supported OCM catalyst. As will be appreciated by one of skill in the art, and with the help of this disclosure, the amount of the OCM catalytic composition on the support, and consequently the amount of support in the catalyst composition, can depend on the catalytic activity of the OCM catalytic composition.

In alternative aspects, the supported OCM catalyst can have a weight ratio of the OCM catalytic composition to the support is in a range of from about 0.01 to about 2.0, alternatively in a range of from about 0.05 to about 1.0, or alternatively in a range of from about 0.1 to about 0.6.

The supported OCM catalyst can have a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc.

The supported OCM catalyst can have a crush strength in a range of from about 1 N to about 800 N, alternatively in a range of from about 2 N to about 400 N, or alternatively in a range of from about 3 N to about 100 N.

The supported OCM catalyst as disclosed herein can be made by using any suitable methodology. In an aspect, the supported OCM catalyst is prepared by contacting a support with an OCM catalytic composition of the type described herein. In an aspect, the supported OCM catalyst is prepared by contacting a support with one or more components of an OCM catalytic composition of the type described herein. In an aspect, the supported OCM catalyst is prepared by contacting a support with one or more components (e.g., one or more metal compounds in solution such as an OCM catalytic precursor mixture) of an OCM catalytic composition of the type described herein.

In an aspect, a method of making an OCM catalyst composition can comprise a step of forming or otherwise obtaining an OCM catalytic precursor mixture (e.g., an aqueous solution); wherein the OCM catalytic precursor mixture comprises one or more compounds comprising an alkaline earth metal (A) cation, one or more compounds comprising a first rare earth element (Z) cation, one or more compounds comprising a second rare earth element (E) cation, and one or more compounds comprising a redox agent or a third rare earth element (D) cation; and wherein the first rare earth element cation, the second rare earth element cation, and the third rare earth element cation, when present, are not the same (i.e., are different). The OCM catalyst precursor mixture is characterized by a molar ratio of first rare earth element to alkaline earth metal of b:1, wherein b is from about 0.1 to about 10.0, alternatively from about 0.3 to about 10.0, alternatively from about 0.5 to about 8, or alternatively from about 1 to about 5. The OCM catalytic precursor mixture can be characterized by a molar ratio of second rare earth element to alkaline earth metal of c:1, wherein c is from about 0.1 to about 10.0, alternatively from about 0.1 to about 8, or alternatively from about 0.5 to about 5. The OCM catalyst precursor mixture can be characterized by a molar ratio of redox agent or third rare earth element to alkaline earth metal of d:1, wherein d is from about 0 to about 10.0, alternatively from about 0.1 to about 8, or alternatively from about 0.5 to about 5.

The one or more compounds comprising an alkaline earth metal cation can comprise an alkaline earth metal nitrate, an alkaline earth metal oxide, an alkaline earth metal hydroxide, an alkaline earth metal chloride, an alkaline earth metal acetate, an alkaline earth metal carbonate, and the like, or combinations thereof. The one or more compounds comprising a first rare earth element cation can comprise a first rare earth element nitrate, a first rare earth element oxide, a first rare earth element hydroxide, a first rare earth element chloride, a first rare earth element acetate, a first rare earth element carbonate, and the like, or combinations thereof. The one or more compounds comprising a second rare earth element cation can comprise a second rare earth element nitrate, a second rare earth element oxide, a second rare earth element hydroxide, a second rare earth element chloride, a second rare earth element acetate, a second rare earth element carbonate, and the like, or combinations thereof. The one or more compounds comprising a redox agent cation can comprise a redox agent nitrate, a redox agent oxide, a redox agent hydroxide, a redox agent chloride, a redox agent acetate, a redox agent carbonate, and the like, or combinations thereof. The one or more compounds comprising a third rare earth element cation can comprise a third rare earth element nitrate, a third rare earth element oxide, a third rare earth element hydroxide, a third rare earth element chloride, a third rare earth element acetate, a third rare earth element carbonate, and the like, or combinations thereof.

In some aspects, the OCM catalytic precursor mixture can be formed in the presence of water, for example by contacting water or any suitable aqueous medium with one or more compounds comprising an alkaline earth metal (A) cation, one or more compounds comprising a first rare earth element (Z) cation, and optionally one or more compounds comprising a second rare earth element (E) cation and/or one or more compounds comprising a redox agent or a third rare earth element (D) cation. In such aspects, the OCM catalytic precursor mixture comprises water.

In other aspects, the OCM catalytic precursor mixture can be formed in the absence of water (e.g., substantial absence of water; without adding water, etc.), for example by contacting the one or more compounds comprising an alkaline earth metal (A) cation, one or more compounds comprising a first rare earth element (Z) cation, and optionally one or more compounds comprising a second rare earth element (E) cation and/or one or more compounds comprising a redox agent or a third rare earth element (D) cation with each other. In such aspects, the one or more compounds comprising an alkaline earth metal (A) cation, one or more compounds comprising a first rare earth element (Z) cation, and optionally one or more compounds comprising a second rare earth element (E) cation and/or one or more compounds comprising a redox agent or a third rare earth element (D) cation can be mixed together, for example by grinding, dry blending, or otherwise intimately mixing to obtain a homogeneous mixture (e.g., OCM catalytic precursor mixture), and the homogeneous mixture may be further contacted with the support (e.g., mixed together). As will be appreciated by one of skill in the art, and with the help of this disclosure, while the one or more compounds comprising an alkaline earth metal (A) cation, one or more compounds comprising a first rare earth element (Z) cation, and optionally one or more compounds comprising a second rare earth element (E) cation and/or one or more compounds comprising a redox agent or a third rare earth element (D) cation can be mixed without adding water, in some instances, a small amount of water can be added to promote or enable an uniform mixing of the compounds, for example by forming a paste, and the homogeneous mixture may be further contacted with the support (e.g., mixed together). Further, and as will be appreciated by one of skill in the art, and with the help of this disclosure, whether water is used or not for forming the OCM catalyst precursor mixture, the OCM catalyst precursor mixture can be further subjected to a step of drying and/or calcining as disclosed herein.

Without wishing to be limited by theory, some of the one or more compounds comprising an alkaline earth metal (A) cation, one or more compounds comprising a first rare earth element (Z) cation, one or more compounds comprising a second rare earth element (E) cation, one or more compounds comprising a redox agent or a third rare earth element (D) cation, or combinations thereof can be insoluble in water, or only partially soluble in water (e.g., lanthanum oxide, ytterbium oxide, strontium carbonate, neodymium oxide, etc.); and in such instances, these compounds cannot be solubilized in water, but rather mixed as dry materials, or with little water as to (e.g., an amount of water effective to) form a paste (e.g., homogeneous mixture), and the paste (e.g., homogeneous mixture) may be further contacted with the support (e.g., mixed together).

Further, without wishing to be limited by theory, and as will be appreciated by one of skill in the art, and with the help of this disclosure, even when the OCM catalytic precursor mixture is formed without water addition, the OCM catalytic precursor mixture can contain a small amount of water, for example water from atmospheric moisture.

In an aspect, the step of forming the OCM catalytic precursor mixture can comprise solubilizing the one or more compounds comprising an alkaline earth metal cation, one or more compounds comprising a first rare earth element cation, one or more compounds comprising a second rare earth element cation, and one or more compounds comprising a redox agent cation or a third rare earth element cation in an aqueous medium to form an OCM catalytic precursor aqueous solution. The aqueous medium can be water, or an aqueous solution. The OCM catalytic precursor aqueous solution can be formed by dissolving the one or more compounds comprising an alkaline earth metal cation, one or more compounds comprising a first rare earth element cation, one or more compounds comprising a second rare earth element cation, one or more compounds comprising a redox agent cation or a third rare earth element cation, or combinations thereof, in water or any suitable aqueous medium. As will be appreciated by one of skill in the art, and with the help of this disclosure, the one or more compounds comprising an alkaline earth metal cation, one or more compounds comprising a first rare earth element cation, one or more compounds comprising a second rare earth element cation, and one or more compounds comprising a redox agent cation or a third rare earth element cation can be dissolved in an aqueous medium in any suitable order. In some aspects, the one or more compounds comprising an alkaline earth metal cation, one or more compounds comprising a first rare earth element cation, one or more compounds comprising a second rare earth element cation, and one or more compounds comprising a redox agent cation or a third rare earth element cation can be first mixed together and then dissolved in an aqueous medium.

In an aspect, a method of making the supported OCM catalyst comprises contacting an OCM catalytic precursor mixture with a support such that the OCM catalytic precursor mixture is supported by the support to form an impregnated support, and this may also be referred to a metalizing the support. In an aspect, a method of making the supported OCM catalyst comprises contacting a OCM catalytic precursor mixture with a support such that at least a portion of the OCM catalytic precursor mixture contacts, coats, is embedded in, is supported by, and/or is distributed throughout at least a portion of the support to form an impregnated support. In an aspect, a method of making the supported OCM catalyst comprises or consists of a single metallization step (e.g., impregnation of the OCM catalytic precursor mixture on the support) and a single calcination step. Without being limited by theory, it is believed that a single metallization step followed by a single calcination step helps to preserve the crush strength of the resultant supported OCM catalyst.

In an aspect, a method of making the supported OCM catalyst comprises contacting an OCM catalytic precursor aqueous mixture with a support such that the OCM catalytic aqueous precursor mixture is supported by the support to form an impregnated support. In an aspect, a method of making the supported OCM catalyst comprises contacting an OCM catalytic precursor aqueous mixture with a porous support (e.g., alumina-silica) such that at least a portion of the OCM catalytic precursor aqueous mixture contacts, coats, is embedded in, is supported by, and/or is distributed throughout at least a portion of the porous support to form an impregnated support. The OCM catalytic precursor aqueous mixture can be contacted with the support according to any suitable procedure, including but not limited to incipient wetness impreganation, wet impregnation, soaking, ion exchange, coating (dip or spray), or chemical deposition.

In an aspect, a method of making the supported OCM catalyst comprises contacting an OCM catalytic precursor aqueous mixture with a porous support (e.g., alumina-silica), wherein the contacting is performed via incipient wetness impregnation (also called capillary impregnation or dry impregnation) with an aqueous solution comprising the OCM catalytic composition to form an impregnated support. With incipient wetness impregnation, capillary action draws the solution into the pores, and thus an amount of the OCM catalytic precursor aqueous mixture added to the support is typically equal to or less than the total pore volume of the support. Where the amount of OCM catalytic precursor aqueous mixture added to the support is less than the total pore volume of the support, multiple contacting steps can be used such that the total amount of OCM catalytic precursor aqueous mixture added to the support is about equal to the total pore volume of the support. OCM catalytic precursor aqueous mixture added in excess of the support pore volume may cause the solution transport to change from a capillary action process to a diffusion process, which can slow the impregnation process. The loading of the OCM catalytic composition can be controlled by the concentration of metal ions in solution (e.g., in the OCM catalytic precursor aqueous mixture), which means that the support surface does not play an important role, but merely acts as a physical support. The maximum loading of OCM catalytic composition into the support can be limited by the solubility of the individual components of the OCM catalyst precursor mixture in the solution (e.g., in water). The impregnated support can then be dried and calcined to drive off the volatile components within the solution, depositing the OCM catalytic composition on one or more surfaces of the support (e.g., outer surface and surface of pores).

The impregnated support can be dried to form a dried, impregnated support. In an aspect, the impregnated support can be dried at a temperature ranging from about 75° C. to about 400° C., alternatively ranging from about 80° C. to about 400° C., alternatively ranging from about 100° C. to about 400° C., alternatively ranging from about 125° C. to about 400° C., alternatively ranging from about 75° C. to about 200° C., alternatively ranging from about 80° C. to about 200° C., alternatively ranging from about 100° C. to about 200° C., alternatively ranging from about 125° C. to about 200° C., for a time period of equal to or greater than about 4 hours, alternatively equal to or greater than about 8 hours, or alternatively equal to or greater than about 12 hours, to yield the dried, impregnated support.

In an aspect, a method of making an OCM catalyst composition can comprise a step of calcining at least a portion of the dried, impregnated support to form the supported OCM catalyst, wherein the supported OCM catalyst is characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states. The dried, impregnated support can be calcined at a temperature ranging from about 250° C. to about 1,100° C., alternatively ranging from about 400° C. to about 1,100° C., alternatively ranging from about 750° C. to about 1,100° C., alternatively ranging from about 800° C. to about 1,000° C., or alternatively ranging from about 900° C. to about 1,100° C. for a time period of equal to or greater than about 2 hours, alternatively equal to or greater than about 4 hours, or alternatively equal to or greater than about 6 hours, to yield the supported OCM catalyst.

In some aspects, at least a portion of the dried, impregnated support can be calcined in an oxidizing atmosphere (e.g., in an atmosphere comprising oxygen, for example in air) to form the supported OCM composition. Without wishing to be limited by theory, the oxygen in the OCM catalytic compositions characterized by the general formula $A_aZ_bE_cD_dO_x$ can originate in the oxidizing atmosphere used for calcining the dried, impregnated support. Further, without wishing to be limited by theory, the oxygen in the OCM catalytic compositions characterized by the general formula $A_aZ_bE_cD_dO_x$ can originate in the one or more compounds comprising an alkaline earth metal cation, one or more compounds comprising a first rare earth element cation, one or more compounds comprising a second rare earth element cation, and one or more compounds comprising a redox agent cation or a third rare earth element cation, provided that at least one of these compounds comprises oxygen in its formula, as is the case with nitrates, oxides, hydroxides, acetates, carbonates, etc.

The OCM reactant mixture can be a gaseous mixture. The OCM reactant mixture can comprise a hydrocarbon or mixtures of hydrocarbons, and oxygen. In some aspects, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an aspect, the OCM reactant mixture can comprise $CH_4$ and $O_2$.

The $O_2$ used in the OCM reactant mixture can be oxygen gas (which may be obtained via a membrane separation process), technical oxygen (which may contain some air), air, oxygen enriched air, and the like, or combinations thereof.

The OCM reactant mixture can further comprise a diluent. The diluent is inert with respect to the OCM reaction, e.g., the diluent does not participate in the OCM reaction. In an aspect, the diluent can comprise water (e.g., steam), nitrogen, inert gases, and the like, or combinations thereof. In an aspect, the diluent can be present in the OCM reactant mixture in an amount of from about 0.5% to about 80%, alternatively from about 5% to about 50%, or alternatively from about 10% to about 30%, based on the total volume of the OCM reactant mixture.

The OCM reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an aspect, the OCM reactor can comprise a catalyst bed comprising the supported OCM catalyst.

In an aspect, the OCM reactor can be characterized by any suitable OCM reactor operational parameters, such as temperature (e.g., feed preheat temperature, reactor effluent temperature, etc.), pressure, flow rate (e.g., space velocity), and the like, or combinations thereof.

The OCM reaction mixture can be introduced to the OCM reactor at a temperature (e.g., feed preheat temperature) of from about 150° C. to about 1,000° C., alternatively from about 225° C. to about 900° C., or alternatively from about 250° C. to about 800° C. As will be appreciated by one of skill in the art, and with the help of this disclosure, while the OCM reaction is exothermic, heat input is necessary for promoting the formation of methyl radicals from $CH_4$, as the C—H bonds of $CH_4$ are very stable, and the formation of methyl radicals from $CH_4$ is endothermic. In an aspect, the OCM reaction mixture can be introduced to the OCM reactor at a temperature effective to promote an OCM reaction.

The OCM reactor can be characterized by a reactor effluent temperature of from about 400° C. to about 1,200° C., alternatively from about 500° C. to about 1,100° C., or alternatively from about 600° C. to about 1,000° C.

The OCM reactor can be characterized by a pressure of from about ambient pressure (e.g., atmospheric pressure) to about 500 psig, alternatively from about ambient pressure to about 200 psig, or alternatively from about ambient pressure to about 150 psig. In an aspect, the method for producing olefins as disclosed herein can be carried out at ambient pressure.

The OCM reactor can be characterized by a gas hourly space velocity (GHSV) of from about 500 h$^{-1}$ to about 10,000,000 h$^{-1}$, alternatively from about 500 h$^{-1}$ to about 1,000,000 h$^{-1}$, alternatively from about 500 h$^{-1}$ to about 100,000 h$^{-1}$, alternatively from about 500 h$^{-1}$ to about 50,000 h$^{-1}$, alternatively from about 1,000 h$^{-1}$ to about 40,000 h$^{-1}$, or alternatively from about 1,500 h$^{-1}$ to about 25,000 h$^{-1}$. Generally, the GHSV relates a reactant (e.g., reactant mixture) gas flow rate to a reactor volume. GHSV is usually measured at standard temperature and pressure.

In some aspects, the OCM catalyst composition disclosed herein can be employed in single stage OCM processes. In other aspects, the OCM catalyst composition disclosed herein can be employed in multi-stage OCM processes.

In some aspects, a method for producing olefins as disclosed herein can comprise a single stage or multiple stages (e.g., as part of a multi-stage process), wherein each individual stage can comprise an oxidative coupling of methane (OCM) reactor or reaction zone, and wherein each individual stage can be repeated as necessary to achieve a target methane conversion for the overall multi-stage process. For purposes of the disclosure herein, a stage of a process can be defined as a single pass conversion through a given catalyst bed. Any suitable physical configuration and arrangement of components of a catalyst bed (e.g., catalyst particles, inert media, spacers, support structures, screens, etc.) within the given catalyst bed may be employed. A multi-stage process generally comprises a plurality of individual stages (e.g., a plurality of reaction zones), wherein each individual stage (e.g., reaction zone) comprises a single pass conversion through a given catalyst bed. While the current disclosure will be discussed in detail in the context of a single stage comprising a single reactor comprising a given catalyst bed, it should be understood that any suitable stage/reactor/catalyst bed configurations can be used. For example, two or more stages of a multi-stage process can be housed in one or more reactors. As will be appreciated by one of skill in the art, and with the help of this disclosure, multiple stages can be housed within a single reaction vessel, for example a vessel comprising two or more catalyst beds in series. Further, as will be appreciated by one of skill in the art, and with the help of this disclosure, multiple vessels can be part of a single stage, for example two or more vessels in parallel, wherein a reactant mixture is distributed between and introduced to the two or more vessels in parallel. It should be understood that any suitable number of stages can be used, such as for example, 1 stage, 2 stages, 3 stages, 4 stages, 5 stages, 6 stages, 7 stages, 8 stages, 9 stages, 10 stages, or more stages. Such multi-stage processes may be implemented via a corresponding plurality of reactors in series, as is described herein.

In an aspect, the method for producing olefins as disclosed herein can comprise recovering at least a portion of the product mixture from the OCM reactor, wherein the product mixture can comprise olefins, water, CO, CO$_2$, and unreacted methane. In an aspect, a method for producing olefins as disclosed herein can comprise recovering at least a portion of the olefins from the product mixture. The product mixture can comprise C$_{2+}$ hydrocarbons (including olefins), unreacted methane, and optionally a diluent. The C$_{2+}$ hydrocarbons can comprise C$_2$ hydrocarbons and C$_3$ hydrocarbons. In an aspect, the C$_{2+}$ hydrocarbons can further comprise C$_4$ hydrocarbons (C$_4$s), such as for example butane, iso-butane, n-butane, butylene, etc. The C$_2$ hydrocarbons can comprise ethylene (C$_2$H$_4$) and ethane (C$_2$H$_6$). The C$_2$ hydrocarbons can further comprise acetylene (C$_2$H$_2$). The C$_3$ hydrocarbons can comprise propylene (C$_3$H$_6$) and propane (C$_3$H$_8$).

The water produced from the OCM reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

A method for producing olefins as disclosed herein can comprise recovering at least a portion of the olefins from the product mixture. In an aspect, at least a portion of the olefins can be separated from the product mixture by distillation (e.g., cryogenic distillation). As will be appreciated by one of skill in the art, and with the help of this disclosure, the olefins are generally individually separated from their paraffin counterparts by distillation (e.g., cryogenic distillation). For example, ethylene can be separated from ethane by distillation (e.g., cryogenic distillation). As another example, propylene can be separated from propane by distillation (e.g., cryogenic distillation).

In an aspect, at least a portion of the unreacted methane can be separated from the product mixture to yield recovered methane. Methane can be separated from the product mixture by using any suitable separation technique, such as for example distillation (e.g., cryogenic distillation). At least a portion of the recovered methane can be recycled to the reactant mixture.

In an aspect, the O$_2$ conversion of the OCM reaction as disclosed herein can be equal to or greater than about 90%, alternatively equal to or greater than about 95%, alternatively equal to or greater than about 99%, alternatively equal to or greater than about 99.9%, or alternatively about 100%. Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. As will be appreciated by one of skill in the art, and with the help of this disclosure, the reactant mixture in OCM reactions is generally characterized by a methane to oxygen molar ratio of greater than 1:1, and as such the O$_2$ conversion is fairly high in OCM processes, most often approaching 90%-100%. Without wishing to be limited by theory, oxygen is usually a limiting reagent in OCM processes. The oxygen conversion can be calculated by using equation (V):

$$O_2 \text{ conversion} = \frac{O_2^{in} - O_2^{out}}{O_2^{in}} \times 100\% \quad\quad (V)$$

wherein $O_2^{in}$=number of moles of O$_2$ that entered the OCM reactor as part of the reactant mixture; out and $O_2^{out}$=number of moles of O$_2$ that was recovered from the OCM reactor as part of the product mixture.

In an aspect, the supported OCM catalyst composition as disclosed herein can be characterized by an O$_2$ conversion that is about equal to the O$_2$ conversion of an otherwise similar supported OCM catalyst composition at a reaction temperature of equal to or greater than about 675° C., 700°

Figure 2:
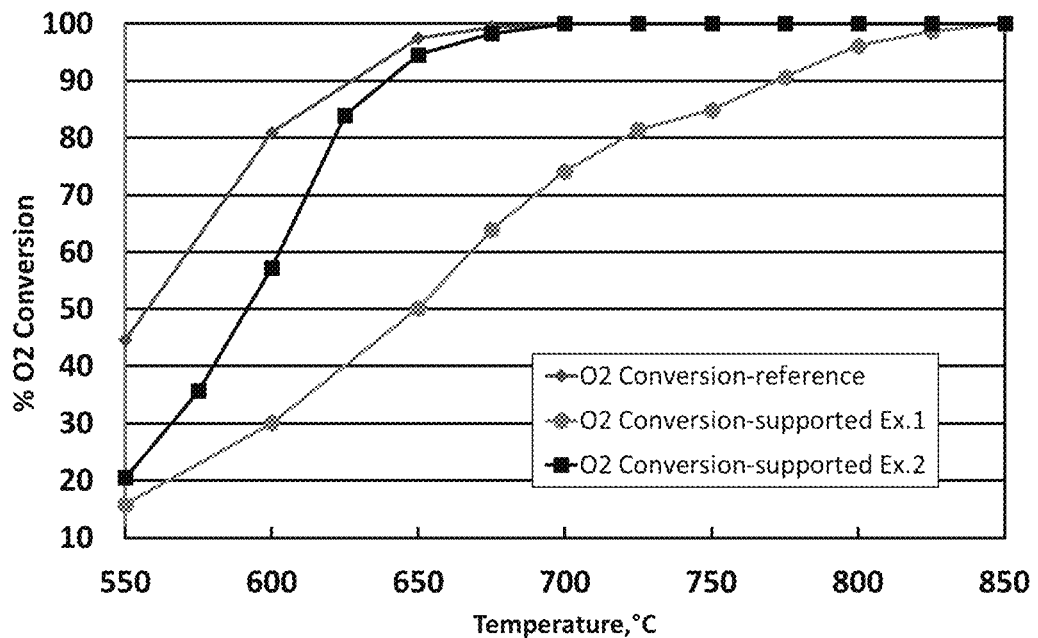
FIG. 2 displays a graph of oxygen conversion as a function of temperature for an oxidative coupling of the methane (OCM) reaction for the Example 1 and 2 supported catalysts and the unsupported reference catalyst #1.

C., 750° C., 800° C., or 850° C., for example as shown in FIG. 2. In an aspect, the supported OCM catalyst disclosed herein has an $O_2$ conversion of equal to or greater than about 90, 95, 98, 99, 99.9, 99.99, or 100% at a reaction temperature of equal to or greater than about 675° C., 700° C., 750° C., 800° C., or 850° C.

In an aspect, the supported OCM catalyst composition as disclosed herein can be characterized by a $C_{2+}$ selectivity that is increased by equal to or greater than about 2.5%, alternatively equal to or greater than about 5%, or alternatively equal to or greater than about 10%, when compared to a $C_{2+}$ selectivity of an otherwise similar unsupported OCM catalytic composition.

Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc.

A $C_{2+}$ selectivity (e.g., selectivity to $C_{2+}$ hydrocarbons) refers to how much $C_2H_4$, $C_3H_6$, $C_2H_2$, $C_2H_6$, $C_3H_8$, and $C_4$s were formed divided by the total products formed, including $C_2H_4$, $C_3H_6$, $C_2H_2$, $C_2H_6$, $C_3H_8$, $C_4$s, $CO_2$ and CO. For example, the $C_{2+}$ selectivity can be calculated by using equation (VI):

$$C_{2+} \text{ selectivity} = \frac{2C_{C_2H_4} + 2C_{C_2H_6} + 2C_{C_2H_2} + 3C_{C_3H_6} + 3C_{C_3H_8} + 4C_{C_{4s}}}{2C_{C_2H_4} + 2C_{C_2H_6} + 2C_{C_2H_2} + 3C_{C_3H_6} + 3C_{C_3H_8} + 4C_{C_{4s}} + C_{CO_2} + C_{CO}} \times 100\% \quad \text{(VI)}$$

As will be appreciated by one of skill in the art, and with the help of this disclosure, if a specific product and/or hydrocarbon product is not produced in a certain OCM reaction/process, then the corresponding $C_{Cx}$ is 0, and the term is simply removed from selectivity calculations.

In an aspect, the supported OCM catalyst composition as disclosed herein can be characterized by a methane conversion that is increased by equal to or greater than about 1%, alternatively equal to or greater than about 2%, or alternatively equal to or greater than about 5%, when compared to a methane conversion of an otherwise similar unsupported OCM catalytic composition. In some aspects, the methane conversion in the presence of a supported OCM catalyst as disclosed herein can be from about 10% to about 60%, alternatively from about 12.5% to about 50%, or alternatively from about 15% to about 45%.

Methane conversion was calculated according to equation (VII). Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. For example, the methane conversion can be calculated by using equation (VII):

$$CH_4 \text{ conversion} = \frac{C_{CH_4}^{in} - C_{CH_4}^{out}}{C_{CH_4}^{in}} \times 100\% \quad \text{(VII)}$$

wherein $C_{CH_4}^{in}$=number of moles of C from $CH_4$ that entered the reactor as part of the reactant mixture; and $C_{CH_4}^{out}$=number of moles of C from $CH_4$ that was recovered from the $CH_4$ reactor as part of the product mixture.

In an aspect, the supported OCM catalyst composition as disclosed herein can be characterized by a $C_{2+}$ yield that is increased by equal to or greater than about 1%, alternatively equal to or greater than about 2%, or alternatively equal to or greater than about 5%, when compared to a $C_{2+}$ yield of an otherwise similar unsupported OCM catalytic composition. In some aspects, the $C_{2+}$ yield in the presence of a supported OCM catalyst as disclosed herein can be from about 10% to about 60%, alternatively from about 12.5% to about 50%, or alternatively from about 15% to about 45%.

Further, a $C_{2+}$ yield can be calculated as the product of $C_{2+}$ selectivity and methane conversion, for example by using equation (VIII):

$$C_{2+} \text{ yield} = \text{methane conversion} \times C_{2+} \text{ selectivity} \quad \text{(VIII)}$$

For example, if a certain OCM reaction/process is characterized by a 50% methane conversion, and by a 50% $C_{2+}$ selectivity, the resulting $C_{2+}$ yield can be calculated as being 25% (=50%×50%).

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Comparative Example

The mechanism of oxidative coupling of methane reaction has been described widely in many publications and can be summarized into the following key steps:

$[O]_s + CH_4 \rightarrow [OH]_s + CH_3$ (1)
$2CH_3 \rightarrow C_2H_6$ (2)
$CH_3 + O_2 \leftrightarrow CH_3O_2$ (3)
$CH_3 + [O]_s \leftrightarrow [CH_3O]_s$ (4)
$2[OH]_s + 1/2O_2 \rightarrow 2[O]_s + H_2O$ (5)
$C_2H_6 + 1/2O_2 \rightarrow C_2H_4 + H_2O$ (6)
$C_2H_4 + 1/2O_2 \rightarrow C_2H_2 + H_2O$ (7)
$C_2H_4 + 5/2O_2 \rightarrow CO + CO_2 + 2H_2O$ (8)

The first step is the activation of methane with the participation of active oxygen sites $[O]_s$, with the formation of methyl radical $CH_3$ and hydroxyl group $[OH]_s$. The gas phase reaction of coupling of methyl radicals to form the coupling product $C_2H_6$ has low activation energy, therefore does not limit reaction rate. The methyl radicals can react with gas phase oxygen to form $CH_3O_2$(step (3)). They can also re-adsorb on to the catalyst surface and react with surface oxygen to form $[CH_3O]_s$ (step (4)). Steps (3) and (4) are the main reactions controlling the selectivity of the different catalysts. Easy removal of methyl radicals from the oxygen centers will result in high $C_{2+}$ selectivity; while at oxygen centers of low metal-O bond energy, oxidation of methyl radicals through $[CH_3O]_s$ leads to formation of COx. Direction of step (3) depends on the temperature, while direction of step (4) depends both on temperature and on catalyst. These O-containing compounds are the precursors of deep oxidation products, such as CO and $CO_2$. Therefore conversions of methyl radicals through step (3) and (4) are the ones of selectivity loss.

As described in reaction steps (1)-(5), OCM reaction starts with methyl radical formation, coupling of which leads to the formation of ethane. Ethane is further converted to ethylene through parallel reactions of thermal dehydrogenation and catalytic oxidative dehydrogenation, step (6). Further dehydrogenation will produce acetylene, as shown in step (7). Some portion of methyl radicals undergoes to deep oxidation through O-containing compounds $CH_3O_2$ and $[CH_3O]_s$ as shown in steps (3) and (4). In addition to the reaction steps (3) and (4), some of the $C_{2+}$ products formed (use $C_2H_4$ as an example) also undergo deep oxidation to form CO and $CO_2$.

The performance of an unsupported catalyst comprising an OCM catalytic composition of the type described herein was evaluated. For example, when an unsupported OCM catalytic composition is scaled-up for commercial application, the unsupported OCM catalytic composition must be formed into catalyst particles that are sized to meet certain process conditions such as pressure drop through a catalyst bed, crush strength, etc. For example, an unsupported OCM catalytic composition can be formed via compression into a pellet with required strength and shape and size. Catalyst pellet strength will be increased with the increase compressing force. With the increase of pellet strength, catalyst density will be increased. With the increase of pellet density, the pore volume of the catalyst will be reduced, which will enhance mass transfer resistance and enhance the reaction rates of the step (3), (4), (7) and (8), resulting in a low performance, as shown in Lee's (Lee et al., *Fuel* 106 (2013) p 851) work.

FIG. 1 shows the effect of density on $C_{2+}$ selectivity for an unsupported OCM catalytic composition $(Sr_{1.0}La_{0.9}Nd_{0.7}Yb_{0.1}Ox)$ that is formed into a commercial catalyst (e.g., pellets formed via compression). As can be seen, as the density of the unsupported OCM catalytic composition increases (corresponding to increased compressive force in form unsupported catalyst pellets), the $C_{2+}$ selectivity decreases. Thus, forming unsupported OCM catalytic compositions into catalyst pellets via application of compressive force adversely effects the performance of the unsupported OCM catalytic composition, e.g., decreasing the $C_{2+}$ selectivity of the unsupported OCM catalytic composition.

As described in more detail herein, the supported OCM catalysts disclosed herein preserve the crystal and/or pore structure of the OCM catalytic composition (see, e.g., FIGS. 6A and 6B), which will enhance the desorption of methyl radicals formed and other $C_{2+}$ products formed, so that the $C_{2+}$ selectivity can be sustained or enhanced in comparison to the unsupported OCM catalytic composition (e.g., FIG. 1). In particular, the supported OCM catalysts disclosed herein have $C_{2+}$ selectivity that is greater than that of a corresponding unsupported OCM catalytic composition for a given density value. That is, the supported OCM catalysts described herein have a selectivity as a function of density that is greater than the data set forth in FIG. 1 for a corresponding unsupported OCM catalytic composition, and in particular the supported OCM catalysts described herein have a $C_{2+}$ selectivity as a function of density that is in a region of FIG. 1 above the line plotted thereon. In an aspect, a line may be plotted through two points on FIG. 1 (e.g., density 0.5, $C_{2+}$ selectivity 80 and density 1, $C_{2+}$ selectivity 76), and the supported OCM catalysts described herein have a C2+ selectivity as a function of density that satisfies the equation: Y>−8X+84, where Y is the $C_{2+}$ selectivity and X is the density of the supported OCM catalyst in g/cc. In an aspect, the supported OCM catalysts described herein have a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc and a C2+ selectivity in a range of from about 74 to about 90%, alternatively from about 75 to about 90%, alternatively from about 76 to about 90%, alternatively from about 77 to about 90%, alternatively from about 78 to about 90%, alternatively from about 79 to about 90%, alternatively from about 80 to 90%, alternatively from about 74 to about 85%, alternatively from about 75 to about 85%, alternatively from about 76 to about 85%, alternatively from about 77 to about 85%, alternatively from about 78 to about 85%, alternatively from about 79 to about 85%, alternatively from about 80 to 85%, alternatively, from about 74 to about 80%, alternatively from about 75 to about 80%, alternatively from about 76 to about 80%, alternatively from about 77 to about 80%, alternatively from about 78 to about 80%, alternatively from about 79 to about 80%, or alternatively equal to or greater than about 74, 75, 76, 77, 78, 79, 80, 81, 82, 83, 84, or 85%. In an aspect, the supported OCM catalysts described herein have a density in a range of from about 0.6 g/cc to about 2.0 g/cc alternatively in a range of from about 0.8 g/cc to about 1.2 g/cc and a selectivity in a range of from about 78 to about 85%, alternatively from about 78% to about 83%, or alternatively from about 78% to about 81%.

The supports disclosed herein provide the required strength, shape, and size to meet the OCM reaction requirements for reactor design conditions, and therefore provide a supported OCM catalyst with required physical properties for commercial applications.

Unsupported Reference Catalyst #1

An unsupported reference catalyst #1 comprising OCM catalytic composition $(Sr_{1.0}La_{0.9}Nd_{0.7}Yb_{0.1}Ox)$ was prepared by using the following procedure: 10.58 g of $Sr(NO_3)_2$, 19.48 g of $La(NO_3)_3.6H_2O$, 15.35 g of $Nd(NO_3)_3.6H_2O$ and 2.26 g of $Yb(NO_3)_3.5H_2O$ are mixed and dissolved into 100 ml water. The mixture obtained is dried at 125° C. overnight. The dried material is then calcined at 900° C. for 6 hours to produce the unsupported $Sr_{1.0}La_{0.9}Nd_{0.7}Yb_{0.1}Ox$ reference catalyst. The reference catalyst #1 was pressed by using Carver Hydraulic Press into a cake and then the cake was crushed and sieved into 35 to 60 mesh for reactor performance test. The density of the reference catalyst #1 is 0.4 g/cc.

Unsupported Reference Catalyst #2

An unsupported reference catalyst #2 was prepared by using the same way as reference catalyst #1, but by using a higher pressure during the cake formation with the Carver Hydraulic Press. The cake obtained was crushed and sieved into 35 to 60 mesh for reactor performance test. The density of the reference catalyst #1 is 1.3 g/cc.

Supported OCM Catalyst Example 1

A supported OCM catalyst comprising OCM catalytic composition ($Sr_{1.0}La_{0.9}Nd_{0.7}Yb_{0.1}Ox$) on a $SiO_2$—$Al_2O_3$ (SA-5205) support was prepared by the following procedure: 1.36 g of $Sr(NO_3)_2$, 2.51 g of $La(NO_3)3.6H_2O$, 1.98 g of $Nd(NO_3)3.6H_2O$, and 0.29 g of $Yb(NO_3)35H_2O$ were mixed and dissolved in 8 mL of DI water. The dissolved nitrates were then added dropwise via incipient wetness to 7.00 g of sized (35/60 mesh) support (SA-5205, Norton Chemical Process Products Corporation) with several drying and impregnating steps. The impregnated material was then dried at 120° C. and followed by calcination at 900° C. for 6 hours to produce the supported OCM catalyst with a 36% loading of the OCM catalytic composition on the support.

Supported OCM Catalyst Example 2

A supported OCM catalyst comprising OCM catalytic composition ($Sr_{0.5}La_{1.8}Nd_{0.7}Yb_{0.1}Ox$) on a $SiO_2$—$Al_2O_3$ (SA-52252) support was prepared by following the same procedure as supported OCM catalyst Example 1, but with different amounts of catalyst composition precursors to get the catalyst composition of $Sr_{0.5}La_{1.8}Nd_{0.7}Yb_{0.1}Ox$. The OCM catalytic composition loading of supported OCM catalyst Example 2 is 40%.

Supported OCM Catalyst Example 3

A supported OCM catalyst comprising OCM catalytic composition ($Sr_{1.0}La_{0.9}Nd_{0.7}Yb_{0.1}Ox$) on a $SiO_2$—$Al_2O_3$ (SA-5205) support was prepared by the following the same procedure as supported OCM catalyst Example 1, but with different amounts of catalyst composition precursors. The OCM catalytic composition loading of supported OCM catalyst Example 3 is 13%.

Supported OCM Catalyst Example 4

A supported OCM catalyst was obtained by calcining the dried supported OCM catalyst Example 3 material at 800° C., rather than 900° C.

Supported OCM Catalyst Example 5

A supported OCM catalyst comprising OCM catalytic composition ($Sr_{1.0}La_{0.9}Nd_{0.7}Yb_{0.1}Ox$) on a $SiO_2$—$Al_2O_3$ (SA-5218, Norton Chemical Process Products Corporation) support was prepared by following the same procedure as supported OCM catalyst Example 3 and with the same amounts of composition precursors. The OCM catalytic composition loading of supported OCM catalyst Example 5 is 13%.

OCM Performance Test Procedure

The catalysts obtained above were performance tested in a 2.3 mm ID quartz tube reactor. The catalysts above were sized to 35 to 60 mesh before loading into the reactor. The reactor was loaded with 20 mg of catalyst. A mixture of methane and oxygen at a fixed $CH_4:O_2$ ratio of 7.4 was fed to the reactor at a total flow rate of 40.0 sccm and under different reactor temperatures. The products obtained from the OCM reaction were analyzed by using an online Agilent 7890 gas chromatograph (GC) with a thermal conductivity detector (TCD) and a flame ionization detector (FID).

Catalyst Crush Strength Test Procedure

The crush strength measurement method following ASTM D4179-01 (Single pellet crushing strength) and ASTM 6175 (Extrudates radial crushing strength) determines the resistance of formed catalysts to compressive force and is applicable to regular catalyst shapes such as tablets, spheres, extrudates, etc. Resulting value is a force applied to highest resistance before the catalyst is crushed. Its unit is N (newton). Each formed catalyst was placed between metal plates of which one moving to the other plate monitoring applying force until the catalyst particle is crushed. The crush test is repeated with reasonable number of catalyst samples and the resulting data were averaged. The average crush strength of equal to or greater than about 1N, 2N, 3N or 4N would be acceptable for use in a commercial process directed to the oxidative coupling of methane reaction.

OCM Performance Test Results at Reactor Temperatures Ranging from about 500° C. to about 850° C.

FIG. 2 shows the oxygen conversion of the Example 1 and 2 supported catalysts and unsupported reference catalyst #1. It can be seen that the Example 1 supported catalyst shows lower activity compared to the unsupported reference catalyst #1. Although supported catalyst Example 1 has the same composition as unsupported reference catalyst #1, Example 1 catalyst contains only 36% of active catalyst composition and the rest 64% is the support material. As a result, lower oxygen conversion is obtained.

Example 2 catalyst has similar catalyst loading as Example 1 catalyst, but with a different composition. With the different composition, higher oxygen conversion is obtained, indicating that by varying catalyst composition, the catalyst activity of supported catalyst can be improved. The oxygen conversion of Example 2 catalyst is very close to that of unsupported reference catalyst #1, as demonstrated in FIG. 2.

Figure 3:
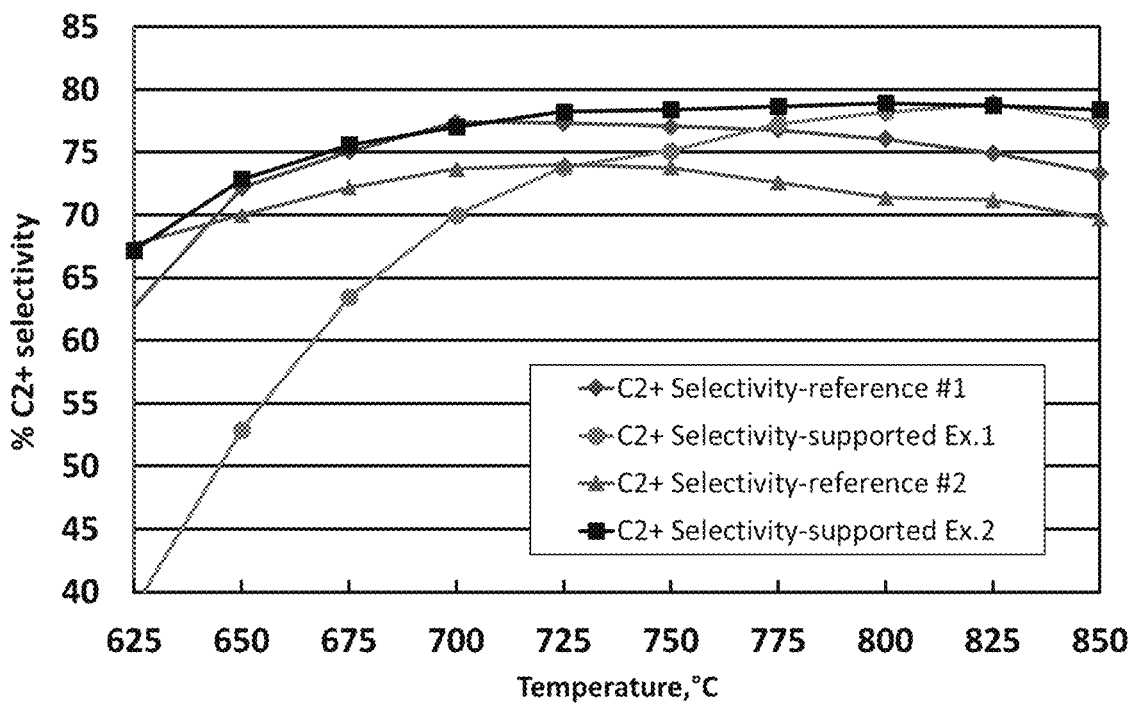
FIG. 3 displays a graph of $C_{2+}$ selectivities as a function of temperature for an OCM reaction for the Example 1 and 2 supported catalysts and the unsupported reference catalysts #1 and #2.

The selectivity comparison of the Example 1 and 2 supported catalysts and unsupported reference catalyst #1 and #2 is shown in FIG. 3. Comparing Example 1 and reference #1 catalysts, at lower temperature, lower $C_{2+}$ selectivity is obtained with Example 1 catalyst, which is related to the lower oxygen conversion as shown in FIG. 2. But when the reactor temperature is higher than 775 C, higher $C_{2+}$ selectivity is obtained with the supported catalyst.

Comparing Example 2 and reference #1 catalysts, Example 2 catalyst demonstrates higher $C_{2+}$ selectivity in the entire reactor temperature range, indicating that by varying the catalyst composition, supported catalyst with higher activity and higher selectivity can be obtained.

Reference #2 catalyst shows lower $C_{2+}$ selectivity than reference #1 catalyst. This is due to the pore structure change when higher pressure is used during the catalyst preparation. Higher pressure reduces pore volume and increases diffusion resistance and increases the diffusion time in the catalyst pore structure, as a result, the deep oxidation reactions are increased and $C_{2+}$ selectivity is reduced. In the high temperature range, the reference #2 catalyst shows 7-8% lower $C_{2+}$ selectivity than Example 1 and 2 catalysts.

This comparison clearly demonstrated that with the supported catalyst invented herein, the optimum open pore structure of the catalyst can be sustained, so that higher selectivity is obtained.

It can also be seen that the supported catalysts demonstrated better $C_{2+}$ selectivity than the reference #1 catalyst, which is only slightly pressure during preparation. This indicates that by loading the catalyst on support as disclosed herein, the supported catalysts may also shorten the diffusion distance, as a result, it lowers the chance for deep oxidation and enhances the $C_{2+}$ selectivity.

Figure 4:
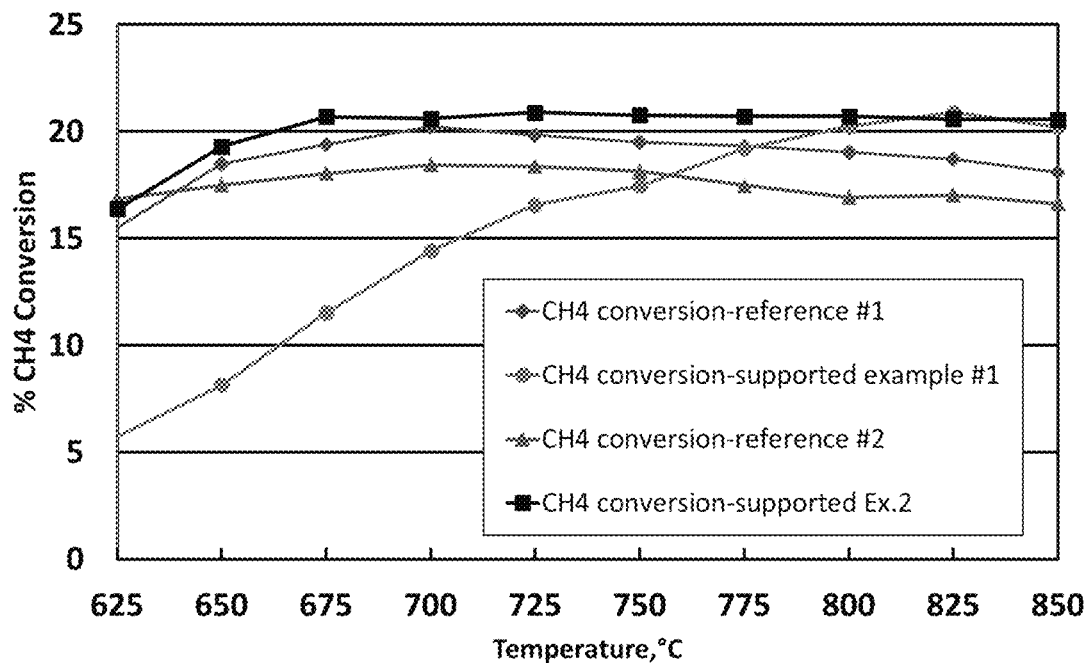
FIG. 4 displays a graph of methane conversion as a function of temperature for an OCM reaction for the Example 1 and 2 supported catalysts and the unsupported reference catalysts #1 and #2.

As we know, under the testing condition with $CH_4$ to $O_2$ ratio of 7.4, oxygen is the limiting agent. With more $CO_2$ formed in the product, because $CO_2$ formation uses more $O_2$ than other products, there will be less oxygen available for $CH_4$ conversion. Therefore, there is less $CH_4$ conversion with the unsupported reference catalysts #1 and #2, compared to the Example 1 and 2 supported catalysts, as shown in FIG. 4.

Figure 5:
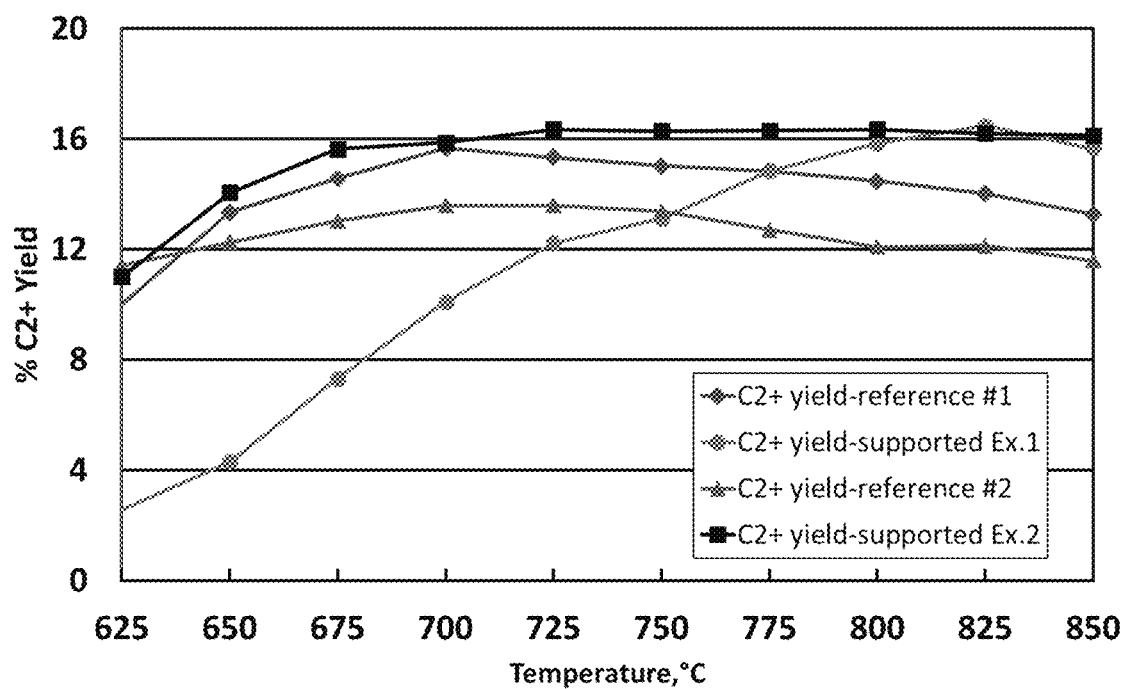
FIG. 5 displays a graph of $C_{2+}$ yield as a function of temperature for an OCM reaction for the Example 1 and 2 supported catalysts and the unsupported reference catalysts #1 and #2.

With higher $CH_4$ conversion and higher $C_{2+}$ selectivity, higher $C_{2+}$ yield will be obtained with the supported catalysts as demonstrated in FIG. 5.

OCM Performance Test Results at Reactor Temperature of 850° C.

Table 1 is a performance comparison of the Example 1-5 supported catalysts and the unsupported reference catalysts #1 and #2 at a reactor temperature of 850° C.

Figure 6A:
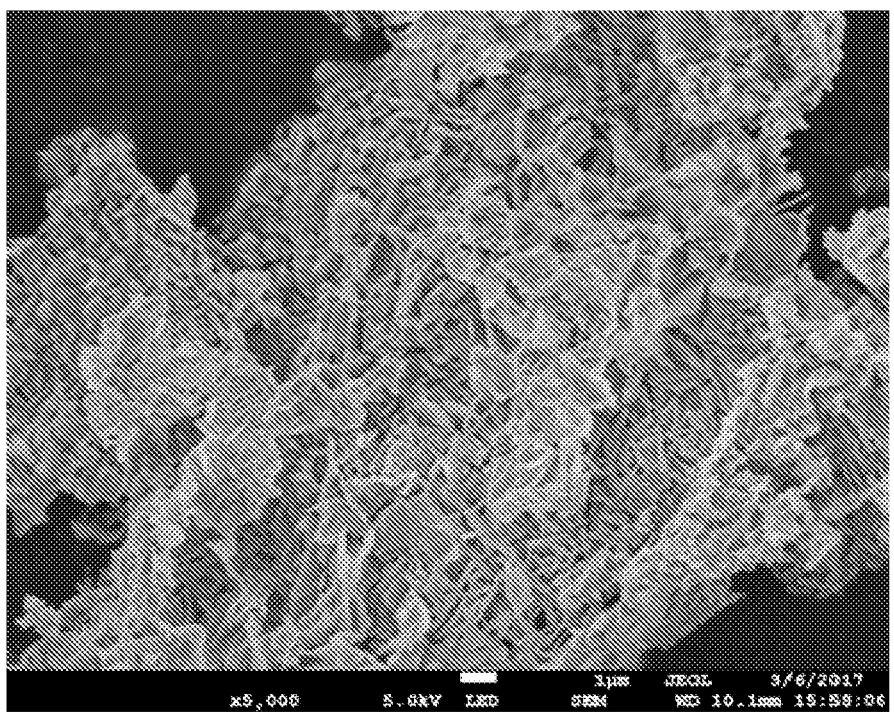
FIGS. 6A and 6B display scan electronic microscopic images (SEM) of the unsupported reference catalyst #1 (non-compressed) and Example 3 supported catalyst, respectively.
Figure 6B:
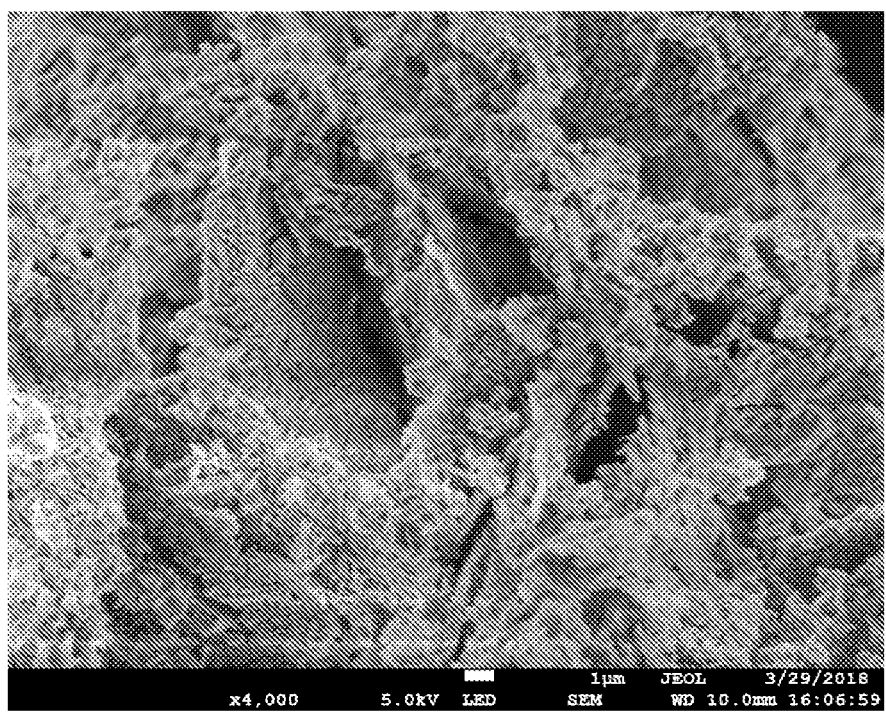

Example 3 supported catalyst is shown in FIGS. 6A and 6B, respectively. It can be seen that the layered crystal structure of the OCM catalytic composition was maintained in the supported catalyst. The layered structure of the crystal and the pore structure associated with it, as shown in FIGS. 6A and 6B, are important for a high performance catalyst. When the catalyst is scaled-up using a compression tableting method (e.g., as shown in unsupported reference catalyst #2), in order to achieve the required tablet strength, certain pressure will be applied to compress the OCM catalytic composition powder. Such compression may break the layered crystals and reduce the pore volume of the OCM catalytic composition. As a result, during the reaction, the reactants, the methyl radial formed or the $C_{2+}$ products formed will take longer time to diffuse in and out from the pore structure and have higher chance to be further converted to deep oxidation products, like $CO_2$. As a result, tableted catalysts (e.g., unsupported reference catalyst #2) will have lower activity and lower selectivity due to the pore structure change. But, with the supported catalyst (e.g., the Example 1-5 supported catalysts), the catalyst crystal structure is not altered, so that the intrinsic performance of the OCM catalyst is maintained.

Catalyst Crush Strength Test

A supported OCM catalyst comprising OCM the same catalytic composition ($Sr_{0.1}La_{1.8}Nd_{0.7}Yb_{0.1}Ox$) on a $SiO_2$—$Al_2O_3$(SA-52252) support was prepared by the following procedure as Example 2. Instead of 35-60 size support, 3 mm sphere support was used (SA-52252, Norton Chemical

TABLE 1

| Performance comparison at 850° C. reactor temperature | | | | | | | |
|---|---|---|---|---|---|---|---|
| | Reference 1 (d = 0.4) | Reference 2 (d = 1.3) | Example 1 | Example 2 | Example 3 | Example 4 | Example 5 |
| $C_{2-}$ | 35.4 | 33.3 | 37.8 | 39.4 | 35.4 | 34.7 | 35.2 |
| $C_2$ | 32.7 | 32.0 | 33.1 | 32.9 | 33.5 | 32.9 | 33.1 |
| $C_{3-}$ | 2.8 | 2.3 | 3.2 | 3.3 | 3.0 | 2.9 | 2.8 |
| $C_3$ | 0.9 | 0.8 | 1.5 | 1.1 | 1.5 | 1.4 | 1.5 |
| $C_{2+}$ | 73.4 | 69.7 | 77.4 | 78.4 | 75.2 | 73.7 | 74.3 |
| CO | 3.9 | 4.0 | 4.6 | 3.5 | 7.3 | 7.1 | 7.5 |
| $CO_2$ | 22.8 | 26.2 | 17.9 | 18.1 | 17.5 | 19.2 | 18.2 |
| $CH_4$ conversion | 18.1 | 16.6 | 20.2 | 20.6 | 19.9 | 19.2 | 19.6 |
| Y($C_{2+}$ yield) | 13.3 | 11.6 | 15.6 | 16.1 | 15.3 | 14.2 | 14.6 |

From the data in Table 1, it can be seen that the Example 1-5 supported catalysts produce higher $C_{2+}$ selectivities than unsupported reference catalysts #1 and much higher than unsupported reference catalysts #2. The higher $C_{2+}$ selectivity come from the lower $CO_2$ selectivity than the unsupported catalyst, especially compared to unsupported reference catalysts #2, which is due to the more deep oxidation from the unsupported reference catalysts #2. Higher $CH_4$ conversions are obtained with supported examples as well. As a result, higher $C_{2+}$ yields are obtained from the supported examples.

Combining the results shown in FIGS. 2, 3, 4 and 5 and the data of Example 2 shown in Table 1, it can be seen that by tuning the catalyst composition, supported catalyst activity can be improved. In addition, the catalyst selectivity can be further improved as well, as a result, $CH_4$ conversion and $C_{2+}$ yield can be improved further.

The scan electronic microscopic images (SEM) of the unsupported reference catalyst #1 (lightly-compressed) and Process Products Corporation). The impregnated material was then dried at 120° C. and followed by calcination at 900° C. for 6 hours to produce the supported OCM catalyst with a 25% loading of the OCM catalytic composition on the support. The crush strength of the 3 mm sphere catalyst obtained was tested and compared with the support as shown in Table 2 below.

TABLE 2

| Crush strength of support and supported catalyst | |
|---|---|
| | Mechanical strength (N) |
| Support | 58 |
| Supported catalyst | 95 |

It can be seen, the supported catalyst developed in this invention does not reduce the mechanical strength, actually, the mechanical strength is increased by some degree.

Silica-alumina supports, like the supports used in this application, are commonly used for preparation for supported catalysts. One issue of this type of support is that if multiple calcination steps with high temperatures, like the temperature used for OCM catalysts, are used, the mechanical strength of the catalyst will be weakened significantly. Sometime, the mechanical strength is so low that it cannot be used in industrial reactors. The novel catalysts of the present disclosure use only one calcination step, so that the catalyst mechanical integrity is not impacted. As a result, with the novel catalysts disclosed herein, high activity, high selectivity, high yield and high mechanical strength catalyst can be obtained, which can be used in industrial reactors.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A supported oxidative coupling of methane (OCM) catalyst comprising a support and an OCM catalytic composition characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states, wherein the supported OCM catalyst has a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc and wherein the catalyst has a $C_{2+}$ selectivity that satisfies the equation: Y>−8X+84, where Y is the $C_{2+}$ selectivity and X is the density of the supported OCM catalyst in g/cc.

2. The supported OCM catalyst of claim 1, wherein the support has a surface area in a range of from greater than zero and less than about 20.0 $m^2/g$, alternatively in a range of from greater than zero and less than about 10.0 $m^2/g$, or alternatively in a range of from greater than zero and less than about 5.0 $m^2/g$, as determined by measuring nitrogen adsorption according to the Brunauer, Emmett and Teller (BET) method.

3. The supported OCM catalyst of claim 1, wherein the support has a total pore volume in a range of from about 0.1 cc/g to about 1.0 cc/g, alternatively in a range of from about 0.15 cc/g to about 0.8 cc/g, or alternatively in a range of from about 0.2 cc/g to about 0.6 cc/g, as determined by measuring nitrogen adsorption according to the BET method.

4. The supported OCM catalyst of claim 1, wherein the support has a pore size distribution in a range of from about 0.01 microns to about 500 microns, alternatively in a range of from about 0.1 microns to about 100 microns, or alternatively in a range of from about 0.5 microns to about 50 microns, as determined by measuring nitrogen adsorption according to the BET method.

5. The supported OCM catalyst of claim 1, wherein the support is a low acidity support.

6. The supported OCM catalyst of 1, having a crush strength in a range of from about 1 N to about 800 N, alternatively in a range of from about 2 N to about 400 N, or alternatively in a range of from about 3 N to about 100 N.

7. The supported OCM catalyst of claim 1, wherein the support is selected from the group consisting of alumina, silica-alumina, silica carbide, zirconia ($ZrO_2$), titania ($TiO_2$), magnesium oxide (MgO), zeolites, transition metal oxides, alkali metal oxides, alkaline earth metal oxides, lanthanide oxides, actinide oxides, carbon, and combinations thereof.

8. The supported OCM catalyst of claim 7, wherein the support comprises silica-alumina and wherein the support is characterized by a weight ratio of silica to alumina ($SiO_2/Al_2O_3$) of equal to or greater than about 100.

9. The supported OCM catalyst of claim 1, wherein the weight ratio of the OCM catalytic composition to the support is in a range of from about 0.01 to about 2.0, alternatively in a range of from about 0.05 to about 1.0, or alternatively in a range of from about 0.1 to about 0.6.

10. The supported OCM catalyst of claim 1, wherein alkaline earth metal is selected from the group consisting of magnesium (Mg), calcium (Ca), strontium (Sr), barium (Ba), and combinations thereof.

11. The supported OCM catalyst of claim 1, wherein the first rare earth element is selected from the group consisting of lanthanum (La), neodymium (Nd), promethium (Pm), samarium (Sm), europium (Eu), and combinations thereof.

12. The supported OCM catalyst of claim 1, wherein the second rare earth element and the third rare earth element can each independently be selected from the group consisting of lanthanum (La), scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

13. The supported OCM catalyst of claim 1, wherein the redox agent is selected from the group consisting of manganese (Mn), tungsten (W), bismuth (Bi), antimony (Sb), tin (Sn), cerium (Ce), praseodymium (Pr), and combinations thereof.

14. The supported OCM catalyst of claim 1 comprising one or more oxides of A; one or more oxides of Z; one or more oxides of E; one or more oxides of D; or combinations thereof.

15. The supported OCM catalyst composition of claim 1, wherein the OCM catalytic material has the general formula $Sr_aLa_bE_cD_dO_x$; wherein E is a second rare earth element; wherein D is a third rare earth element; wherein the second rare earth element and the third rare earth element are different; wherein a is 1.0; wherein b is from about 0.1 to about 10.0; wherein c is from about 0.1 to about 10.0; wherein d is from about 0.1 to about 10.0; and wherein x balances the oxidation states.

16. The supported OCM catalyst composition of claim 15, wherein the OCM catalytic material has the general formula $Sr_aLa_bYb_cTm_dO_x$; wherein a is 1.0; wherein b is from about 0.1 to about 10.0; wherein c is from about 0.1 to about 10.0; wherein d is from about 0.1 to about 10.0; and wherein x balances the oxidation states.

17. The supported OCM catalyst composition of claim 15, wherein the OCM catalytic material has the general formula $Sr_aLa_bNd_cYb_dO_x$; wherein a is 1.0; wherein b is from about 0.1 to about 10.0; wherein c is from about 0.1 to about 10.0; wherein d is from about 0.1 to about 10.0; and wherein x balances the oxidation states.

18. A method of making a supported oxidative coupling of methane (OCM) catalyst comprising contacting a support with an OCM catalytic composition characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; and wherein x balances the oxidation states, wherein the supported OCM catalyst has a density in a range of from about 0.3 g/cc to about 4.5 g/cc, alternatively in a range of from about 0.5 g/cc to about 3.0 g/cc, or alternatively in a range of from about 0.8 g/cc to about 2.0 g/cc and wherein the catalyst has a $C_{2+}$ selectivity that satisfies the equation: $Y>-8X+84$, where Y is the $C_{2+}$ selectivity and X is the density of the supported OCM catalyst in g/cc.

19. The method of claim 18 wherein the contacting is performed via incipient wetness impregnation with an aqueous solution comprising the OCM catalytic composition to form an impregnated support, wherein the impregnated support is thermally treated to form the supported OCM catalyst, wherein the thermal treatment comprises drying in a temperature range of from about 80° C. to about 200° C. and calcination in a temperature range of from about 250° C. to about 1,100° C.

20. A method for producing olefins comprising:
(i) introducing a reactant mixture to a reactor comprising the supported OCM catalyst of claim 1, wherein the reactant mixture comprises $CH_4$ and $O_2$;
(ii) allowing at least a portion of the reactant mixture to contact at least a portion of the supported OCM catalyst and react via an OCM reaction to form a product mixture comprising unreacted methane and olefins;
(iii) recovering at least a portion of the product mixture from the reactor; and
(iv) optionally cooling the product mixture, wherein the reactor is operated a temperature in a range of from about 700° C. to about 1000° C., alternatively in a range of from about 750° C. to about 1000° C., alternatively in a range of from about 775° C. to about 950° C., alternatively in a range of from about 775° C. to about 850° C., or alternatively in a range of from about 800° C. to about 900° C., wherein the OCM reaction is characterized by:
(a) a $C_{2+}$ selectivity of equal to or greater than 75%, alternatively equal to or greater than 77%, or alternatively equal to or greater than 79%;
(b) a methane conversion of equal to or greater than 15%, alternatively equal to or greater than 17%, or alternatively equal to or greater than 20%;
(c) a $C_{2+}$ yield of equal to or greater than 12%, alternatively equal to or greater than 14%, or alternatively equal to or greater than 16%; or
(d) combinations of (a), (b), and (c).

* * * * *